US00PP25683P3

(12) United States Plant Patent
Shearman et al.

(10) Patent No.: US PP25,683 P3
(45) Date of Patent: Jul. 7, 2015

(54) ***POA PRATENSIS* PLANT NAMED 'NE-KYB-05-001'**

(50) Latin Name: ***Poa pratensis* L.**
Varietal Denomination: NE-KYB-05-001

(76) Inventors: Robert C. Shearman, Lincoln, NE (US); Terrance P. Riordan, Lincoln, NE (US); Leonard A. Wit, Jr., Bennet, NE (US)

( * ) Notice: Subject to any disclaimer, the term of this patent is extended or adjusted under 35 U.S.C. 154(b) by 0 days.

(21) Appl. No.: 12/460,378

(22) Filed: Jul. 17, 2009

(65) Prior Publication Data

US 2010/0024086 P1 Jan. 28, 2010

Related U.S. Application Data

(60) Provisional application No. 61/135,114, filed on Jul. 17, 2008.

(51) Int. Cl.
*A01H 5/12* (2006.01)

(52) U.S. Cl.
USPC ..... Plt./393
CPC ..... *A01H 5/12* (2013.01)

(58) Field of Classification Search
USPC ..... Plt./393
CPC ..... A01H 5/12
See application file for complete search history.

*Primary Examiner* — Kent L Bell

(57) ABSTRACT

A new and distinct variety of Kentucky Bluegrass named 'NE-KYB-05-001' (trade name Bella), is characterized by its vegetative only propagation, improved shade and drought tolerance, dwarf-like and dense growth habit, dark green foliage and shorter leaves compared to other Kentucky bluegrass varieties.

4 Drawing Sheets

Latin name of the genus and species: The Latin name of the genus and species of the novel variety disclosed herein is *Poa pratensis* L.

Variety denomination: The inventive variety of *Poa pratensis* L. disclosed herein has been given the variety denomination 'NE-KYB-05-001'.

BACKGROUND OF THE INVENTION

The present invention relates to a new and distinct perennial variety of *Poa pratensis* L.

'NE-KYB-05-001' results from a University breeding program. The parent grasses are unknown. In 1980, Bella was selected from progeny that were derived from crosses made between five female sources (male-emasculated plants) and five male sources of Kentucky bluegrass (*Poa pratensis* L.). Parents were selected based on their turfgrass color and quality characteristics from low maintenance (i.e. minimal fertility and no irrigation) utility turfs that had not been seeded or renovated in the preceding twenty years. Seeds were collected from the female plants and bulked. The bulked seeds were germinated in flats in the greenhouse and seedling plants were transplanted into two inch peat pots. Plants were allowed to develop for about two months. Mature plants were transplanted to the field in an unmowed, space-planting nursery with two foot centers. Progenies were evaluated for turfgrass color, turfgrass quality, plant height, and lateral spread. Bella was selected from the progeny based on its dark green color (RHS 135B), low growth habit, superior lateral spread (i.e. sod forming characteristic) and turfgrass quality characteristics. After being selected at the breeding program, 'NE-KYB-05-001' has been vegetatively propagated via sprigs, rhizomes, plantlets, and/or sod in Nebraska near Mead and Lincoln. Being a poor seed producer is one of the reasons that makes 'NE-KYB-05-001' a unique and different type of *Poa pratensis* L; other characteristics that makes 'NE-KYB-05-001' unique are low plant height, short leaf length, improved shade and drought tolerance. It is anticipated that the plant of this invention will be marketed under the synonym Bella as a trade name. 'NE-KYB-05-001' is so identified in pictures and morphological and agronomic charts of this disclosure.

SUMMARY OF THE INVENTION

'NE-KYB-05-001' is a distinctive variety of *Poa pratensis* L. being a dark green (RHS 135B), extremely low-growing Kentucky bluegrass cultivar, having superior high temperature adaptation and drought resistance. 'NE-KYB-05-001' is a very poor seed producer, making it suitable for vegetative reproduction only, such as sprigs, rhizomes, plantlets, or sod. 'NE-KYB-05-001' is adapted for use in the cool-humid, cool-arid areas in the US and Canada, zones 2 to 7 of the Plant Heat Zone Map, and transition zone 8 (FIG. 1).

DESCRIPTION OF THE NEW VARIETY

Figure 1:
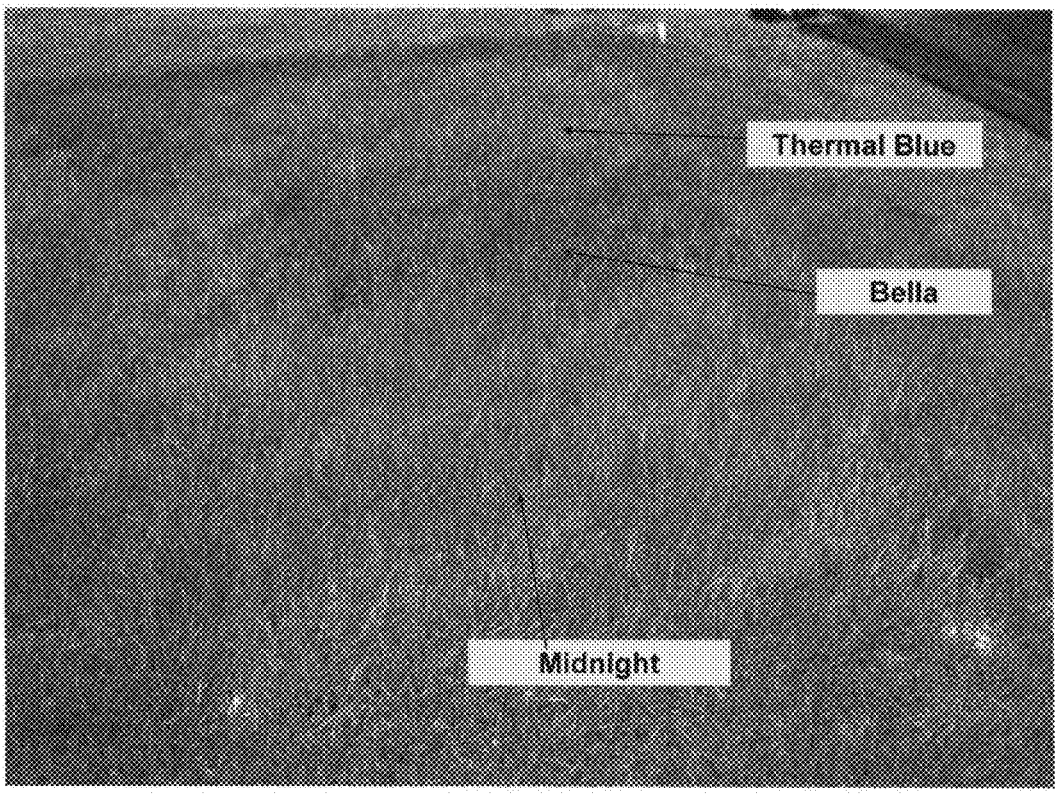
FIG. 1: 'NE-KYB-05-001' in a shade study at a research area in Mead, Nebr.

The following is a detailed description of the new grass variety, based upon observations of the plant grown in field plots at a research area located near Mead, Nebr. 'NE-KYB-05-001' is an outstanding Kentucky bluegrass cultivar that is drought resistant and tolerant of high temperatures. Its drought resistance characteristics make it suited for use where water conservation is an issue. Its heat tolerance makes it suitable for use in the transition zone. 'NE-KYB-05-001' is low-growing and requires infrequent mowing, making it an excellent choice for lawns which can benefit from reduced mowing schedule and for sites that are difficult to mow, such as slopes and banks. 'NE-KYB-05-001' requires low fertilizer input and grows well on soils ranging from sand to heavy clay. 'NE-KYB-005-001' can only be established vegetatively by sprigs, rhizomes, plugs or sod. 'NE-KYB-05-001' has also an excellent shade tolerance compared to other bluegrasses. Its dark green color (RHS 135B) and low growth habit give it a highly appealing turfgrass quality and appearance.

Growth Habit and Dimensions

'NE-KYB-05-001' was compared to 19 other cultivars of Kentucky bluegrass in a study planted located near Mead, Nebr. starting in September 2005. Treatments for all cultivars were the same.

The Analysis of Variance (ANOVA) indicated that cultivars differed significantly for most variables measured (Table 1). Cultivars were quite similar in days to flowering, but 'NE-KYB-05-001' flowered later than 'Blue Moon', 'Absolute', and 'Kenblue' (Table 2). 'NE-KYB-05-001' is a low growing cultivar. It had the lowest foliage height of any of the cultivars studied (Table 2). 'NE-KYB-05-001' had nearly half the plant foliage height of the nearest low growing cultivar. In addition to the low foliage height, 'NE-KYB-05-001' had the shortest leaf length of any of the cultivars (Table 2).

'NE-KYB-05-001' has a dwarf-like growth habit, which would require less frequent mowing. 'NE-KYB-05-001' ranked intermediate in leaf width with 'Princeton 105' having greater leaf width and 'Park' having finer leaf width. Even though 'NE-KYB-05-001' has a dwarf-like growth habit, it still ranked among the cultivars with the greatest amount of plant spread (Table 2). 'NE-KYB-05-001', 'Absolute', and 'NuDensity' had the lowest incidence of stem rust [*Puccinia graminis* f.sp. *poae* (Pers.)], which was the only disease that occurred during this study.

'NE-KYB-05-001' does not readily produce flowers and had the lowest seed yield (110 lbs acre$^{-1}$) of the cultivars studied, and it had the poorest seed germination (12%) (Table 3). Both of these characteristics make it impractical to produce 'NE-KYB-05-001' as a seeded cultivar; therefore 'NE-KYB-05-001' has to be reproduced vegetatively. 'NE-KYB-05-001' and 'Absolute' had the shortest panicle length, and 'NE-KYB-05-001' had the lowest flag leaf height, and shortest flag leaf length of the cultivars studied (Table 3).

TABLE 1

Analysis of Variance for Kentucky bluegrass cultivar comparisons with 'NE-KYB-05-001' conducted during the 2005 to 2007 growing seasons.

| | | Mean Squares of the traits | | | | |
|---|---|---|---|---|---|---|
| Source | df | HD† (days) | FD (days) | FH (cm) | LL (cm) | LW (cm) |
| Rep | 2 | 6.07 | 45.2 | 55.6 | 12.1 | 0.0006 |
| Variety | 19 | 90.5 | 24.7 | 141.2** | 34.9** | 0.002** |
| Error | 38 | 17.9 | 7.3 | 15.1 | 2.6 | 0.0003 |
| CV | | 4.1 | 2.4 | 12.4 | 9.1 | 3.9 |

TABLE 1-continued

Analysis of Variance for Kentucky bluegrass cultivar comparisons with 'NE-KYB-05-001' conducted during the 2005 to 2007 growing seasons.

| | Mean Squares of the traits | | | | | |
|---|---|---|---|---|---|---|
| HD† Source | PL (cm) | PS (cm) | FLH (cm) | FLL (cm) | FLW (cm) | SR (1-9) |
| Rep | 4.48 | 20.42 | 3.88 | 15.93 | 0.013 | 3.03 |
| Variety | 6.79** | 6.28** | 48.71** | 8.65** | 0.007* | 1.44** |
| Error | 0.9 | 2.8 | 7.5 | 3.0 | 0.003 | 0.3 |
| CV | 9.9 | 11.4 | 17.7 | 25.2 | 9.7 | 18.2 |

HD—Heading Date (days to heading), FD—Flowering Date (days to flowering), FH—Foliage Height (cm), LL—Leaf Length (cm), LW—Leaf Width (cm), PL—Panicle Length (cm), PS—Plant Spread (cm), FLH—Flag Leaf Height (cm), FLL—Flag Leaf Length (cm), FLW—Flag Leaf Width (cm), and SR—Stem Rust (1-9 visual rating with 1 = 0-10% and 9 = 90-100% disease incidence).

*Significant at 5% level

**Significant at 1% level

TABLE 2

Kentucky bluegrass cultivar comparisons with 'NE-KYB-05-001' conducted during the 2005 to 2007 growing season.

| No | Variety | HD (days) | FD (days) | FH (cm) | LL (cm) | LW (cm) | PS (cm) | Stem Rust (1-9) |
|---|---|---|---|---|---|---|---|---|
| 1 | 'Absolute' | 99 | 108 | 30.3 | 16.80 | 0.47 | 14.8 | 1.9 |
| 2 | 'NE-KYB-05-001' | 108 | 115 | 13.3 | 9.20 | 0.47 | 15.4 | 1.9 |
| 3 | 'Blue Moon' | 98 | 109 | 31.7 | 17.20 | 0.45 | 14.9 | 3.9 |
| 4 | 'Caliber' | 97 | 115 | 48.9 | 25.80 | 0.48 | 16.9 | 3.0 |
| 5 | 'Common 98/80' | 98 | 114 | 37.3 | 19.60 | 0.45 | 15.1 | 3.6 |
| 6 | 'Everest' | 109 | 116 | 25.1 | 14.10 | 0.45 | 13.2 | 4.3 |
| 7 | 'Everglade' | 111 | 116 | 29.5 | 16.50 | 0.44 | 13.6 | 2.6 |
| 8 | 'Impact' | 106 | 113 | 28.7 | 16.30 | 0.44 | 11.8 | 2.5 |
| 9 | 'Kenblue' | 92 | 106 | 39.3 | 22.40 | 0.44 | 17.1 | 3.6 |
| 10 | 'Liberator ' | 105 | 112 | 26.5 | 15.50 | 0.45 | 14 | 3.3 |
| 11 | 'Midnight' | 93 | 113 | 31.8 | 20.80 | 0.43 | 17.1 | 3.0 |
| 12 | 'NuBlue' | 102 | 116 | 35.4 | 20.10 | 0.44 | 15.4 | 3.9 |
| 13 | 'NuDensity' | 104 | 113 | 30.8 | 16.00 | 0.43 | 13.7 | 1.9 |
| 14 | 'NuGlade' | 107 | 115 | 27.6 | 16.30 | 0.45 | 12.4 | 3.3 |
| 15 | 'Park' | 97 | 113 | 36.4 | 19.80 | 0.42 | 15.1 | 3.2 |
| 16 | 'Perfection' | 111 | 119 | 29.8 | 16.90 | 0.44 | 15.4 | 2.5 |
| 17 | 'Princeton P-105' | 103 | 113 | 34.2 | 20.30 | 0.52 | 14.6 | 2.4 |
| 18 | 'Rugby II' | 100 | 112 | 34.9 | 17.00 | 0.45 | 14.6 | 3.4 |
| 19 | 'Total Eclipse' | 105 | 112 | 27.9 | 15.90 | 0.43 | 13.4 | 3.3 |
| 20 | 'Tsunami' | 104 | 113 | 30.8 | 16.90 | 0.43 | 13.6 | 3.3 |
| | LSD (5%) | 6.9 | 4.5 | 6.4 | 2.7 | 0.03 | 2.8 | 0.9 |

†HD—Heading Date (days to heading), FD—Flowering Date (days to flowering), FH—Foliage Height (cm), LL—Leaf Length (cm), LW—Leaf Width (cm), PS—Plant Spread (cm), and SR—Stem Rust (1-9 visual rating with 1 = 0-10% and 9 = 90-100% disease incidence)

TABLE 3

Kentucky bluegrass cultivar comparisons with 'NE-KYB-05-001' conducted during the 2005 to 2007 growing seasons.

| No | Variety | PL (cm) | FLH (cm) | FLL (cm) | FLW (cm) | SY (lbs acre$^{-1}$) | PB (%) |
|---|---|---|---|---|---|---|---|
| 1 | 'Absolute' | 7.6 | 14.0 | 5.1 | 0.59 | 650 | 92 |
| 2 | 'NE-KYB-05-001' | 7.6 | 10.2 | 3.5 | 0.59 | 110 | 12 |
| 3 | 'Blue Moon' | 9.7 | 12.6 | 6.2 | 0.53 | 810 | 92 |
| 4 | 'Caliber' | 14.9 | 24.7 | 9.3 | 0.54 | 711 | 92 |
| 5 | 'Common 98/80' | 9.9 | 20.7 | 8.0 | 0.49 | 749 | 85 |

TABLE 3-continued

Kentucky bluegrass cultivar comparisons with 'NE-KYB-05-001' conducted during the 2005 to 2007 growing seasons.

| No | Variety | PL (cm) | FLH (cm) | FLL (cm) | FLW (cm) | SY (lbs acre$^{-1}$) | PB (%) |
|---|---|---|---|---|---|---|---|
| 6 | 'Everest' | 8.4 | 11.2 | 5.7 | 0.59 | 668 | 92 |
| 7 | 'Everglade' | 8.7 | 11.8 | 6.8 | 0.59 | 679 | 88 |
| 8 | 'Impact' | 9.2 | 19.2 | 8.1 | 0.55 | 839 | 80 |
| 9 | 'Kenblue' | 9.9 | 21.7 | 7.3 | 0.45 | 767 | 85 |
| 10 | 'Liberator' | 8.6 | 13.0 | 6.0 | 0.53 | 709 | 90 |
| 11 | 'Midnight' | 9.9 | 16.9 | 7.0 | 0.47 | 279 | 90 |
| 12 | 'MN Park' | 9.6 | 19.3 | 7.6 | 0.49 | 630 | 88 |
| 13 | 'NuBlue' | 9.0 | 15.5 | 5.3 | 0.49 | 813 | 90 |
| 14 | 'NuDensity' | 8.6 | 12.2 | 7.2 | 0.58 | 875 | 88 |
| 15 | 'NuGlade' | 9.2 | 13.6 | 6.4 | 0.61 | 788 | 85 |
| 16 | 'Perfection' | 9.0 | 13.4 | 7.0 | 0.57 | 850 | 85 |
| 17 | 'Princeton P-105' | 10.5 | 12.2 | 11.9 | 0.59 | 360 | 92 |
| 18 | 'Rugby II' | 9.5 | 16.5 | 7.3 | 0.59 | 868 | 78 |
| 19 | 'Total Eclipse' | 9.9 | 14.3 | 6.5 | 0.53 | 790 | 75 |
| 20 | 'Tsunami' | 8.6 | 14.3 | 6.2 | 0.54 | 573 | 92 |
| | LSD (5%) | 1.5 | 4.5 | 2.9 | 0.09 | 151 | 14 |

†PL—Panicle Length (cm), FLH—Flag Leaf Height (cm), FLL—Flag Leaf Length (cm), FLW—Flag Leaf Width (cm), SY—Seed Yield (lbs acre-1) and PG—Percent Germination (%)

Drought Tolerance

'NE-KYB-05-001' was tested and compared with 22 other Kentucky bluegrass cultivars in a turfgrass evaluation experiment initiated on September 5 at a research facility located near Mead, Nebr. Irrigation was performed at a 60% ET deficit level to evaluate cultivar performance under drought stress conditions. Normal irrigation for Kentucky bluegrasses in this region is generally conducted at ETp around 80-90%.

The 2006 growing season was the establishment year for this study. 'NE-KYB-05-001' had the second lowest density rating during the establishment year (Table 4). This was a result of the other cultivars being seeded and 'NE-KYB-05-001' being established from vegetative sprigs. Seeding gave the other cultivars an advantage during the establishment year. Despite low density ratings during establishment year, 'NE-KYB-05-001' had the highest quality ratings in September and November, and the second highest quality rating scores in July and August. In addition to that, 'NE-KYB-05-001' had the highest green color rating (scale 1-9, with 9=most green) for all of the cultivars evaluated (Table 4). With its natural and unique dark green color (RHS 135B) 'NE-KYB-05-001' will require less Nitrogen to maintain the same level of green color compared to other bluegrasses.

In 2007, 'NE-KYB-05-001' had spring density ratings that exceeded many varieties (Table 5). Its summer density ratings were ranked third along with 'Perfection' and 'Caliber'. These results support 'NE-KYB-05-001' as a cultivar that is capable of producing a dense high quality turf. 'NE-KYB-05-001' consistently ranked among the highest in turfgrass quality ratings during the 2007 growing season (Table 5). This trend continued in the 2008 growing season where 'NE-KYB-05-001' had the highest ratings for spring green up, for spring and summer density; and for quality for May and June (Table 6). 'NE-KYB-05-001' forms a high quality, dense, dark green turf even under deficit irrigation conditions (60% ET), demonstrating to have a high level of drought tolerance.

TABLE 4

Mean turfgrass color, density, and quality ratings for Kentucky bluegrass cultivar evaluation study. Data are from 2006.

| | Color | Density | Quality | | | |
|---|---|---|---|---|---|---|
| Cultivars | Aug. | Aug. | Jul. | Aug. | Sep. | Nov. |
| 'Absolute' | 6.7 | 9.0 | 6.7 | 5.7 | 6.3 | 5.0 |
| 'NE-KYB-05-001' | 9.0 | 7.3 | 8.3 | 7.7 | 8.3 | 7.0 |
| 'Blue Chip' | 7.0 | 8.7 | 6.7 | 6.0 | 5.0 | 4.3 |
| 'Blue Moon' | 7.3 | 9.0 | 7.3 | 6.7 | 6.7 | 5.3 |
| 'Caliber' | 5.7 | 9.0 | 5.0 | 4.7 | 5.3 | 4.0 |
| 'Common' | 6.0 | 8.7 | 5.7 | 5.3 | 6.0 | 4.7 |
| 'Everest' | 9.0 | 8.7 | 8.3 | 8.0 | 8.0 | 6.7 |
| 'Everglade' | 8.3 | 9.0 | 8.0 | 7.0 | 6.0 | 6.0 |
| 'Impact' | 8.7 | 9.0 | 8.0 | 7.7 | 8.0 | 5.3 |
| 'Kenblue' | 5.3 | 6.0 | 4.3 | 6.7 | 3.7 | 4.3 |
| 'Liberator' | 8.7 | 8.0 | 8.3 | 8.0 | 8.0 | 6.3 |
| 'Limousine' | 6.7 | 9.0 | 6.0 | 5.0 | 4.7 | 3.0 |
| 'Midnight' | 4.0 | 9.0 | 4.3 | 3.7 | 3.7 | 4.3 |
| 'NuBlue' | 6.7 | 9.0 | 6.7 | 5.3 | 6.0 | 5.7 |
| 'NuDensity' | 8.7 | 9.0 | 8.7 | 7.7 | 8.3 | 6.7 |
| 'NuGlade' | 8.3 | 9.0 | 7.7 | 6.7 | 7.7 | 6.3 |
| 'Park' | 5.3 | 9.0 | 5.0 | 4.7 | 4.7 | 4.0 |
| 'Perfection' | 8.3 | 9.0 | 8.0 | 7.0 | 7.7 | 6.3 |
| 'Princeton P-105' | 8.0 | 9.0 | 7.7 | 7.3 | 6.7 | 6.3 |
| 'Rambo' | 8.7 | 9.0 | 8.0 | 7.7 | 6.7 | 6.0 |
| 'Rugby II' | 7.3 | 9.0 | 6.7 | 5.3 | 6.0 | 5.0 |
| 'Total Eclipse' | 7.3 | 9.0 | 7.3 | 6.3 | 7.3 | 5.7 |
| 'Tsunami' | 7.7 | 9.0 | 8.0 | 8.0 | 7.3 | 6.7 |
| LSD (5%) | 0.6 | 0.5 | 0.7 | 0.6 | 0.8 | 0.5 |

Color visual rating: 1-9 (1= least green and 9 = most green)
Density visual rating: 1-9 (1 = least dense and 9 = most dense)
Quality visual ratings: 1-9 (1 = lowest quality and 9 = highest quality)

TABLE 5

Mean turfgrass density, and quality ratings for Kentucky bluegrass cultivar evaluation. Data are from 2007.

| | Density | | |
|---|---|---|---|
| Cultivar | Spring | Summer | Fall |
| Absolute | 8.0 | 8.3 | 9.0 |
| 'NE-KYB-05-001' | 7.7 | 8.0 | 9.0 |
| 'Blue Chip' | 8.0 | 6.0 | 9.0 |
| 'Blue Moon' | 7.0 | 6.3 | 9.0 |
| 'Caliber' | 7.3 | 8.0 | 8.7 |
| 'Common' | 6.7 | 6.7 | 8.7 |
| 'Everest' | 7.3 | 6.7 | 8.7 |
| 'Everglade' | 7.0 | 7.7 | 9.0 |
| 'Impact' | 7.7 | 7.3 | 9.0 |
| 'Kenblue' | 6.3 | 5.0 | 8.7 |
| 'Liberator' | 8.0 | 8.7 | 9.0 |
| 'Limousine' | 8.7 | 6.7 | 8.7 |
| 'Midnight' | 6.0 | 5.3 | 9.0 |
| 'NuBlue' | 8.0 | 7.7 | 8.7 |
| 'NuDensity' | 7.3 | 7.3 | 8.7 |
| 'NuGlade' | 7.0 | 8.3 | 9.0 |
| 'Park' | 6.3 | 6.3 | 9.0 |
| 'Perfection' | 8.0 | 8.0 | 8.7 |
| 'Princeton P-105' | 7.3 | 6.3 | 8.7 |
| 'Rambo' | 7.3 | 7.0 | 8.7 |
| 'Rugby II' | 7.7 | 7.7 | 9.0 |
| 'Total Eclipse' | 7.3 | 6.7 | 9.0 |
| 'Tsunami' | 7.0 | 8.7 | 9.0 |
| LSD (5%) | 0.9 | 0.5 | ns |

| | Quality | | | | | |
|---|---|---|---|---|---|---|
| Cultivar | Apr. | May | Jul. | Aug. | Sep. | Oct. |
| Absolute | 3.0 | 5.7 | 5.7 | 6.7 | 5.7 | 6.7 |
| 'NE-KYB-05-001' | 4.0 | 7.7 | 7.3 | 7.3 | 7.7 | 7.0 |
| 'Blue Chip' | 2.7 | 6.3 | 5.7 | 5.7 | 5.7 | 6.7 |

TABLE 5-continued

Mean turfgrass density, and quality ratings for Kentucky bluegrass cultivar evaluation. Data are from 2007.

| | | | | | | |
|---|---|---|---|---|---|---|
| 'Blue Moon' | 2.3 | 5.7 | 6.3 | 6.3 | 5.0 | 7.3 |
| 'Caliber' | 2.7 | 5.7 | 6.0 | 6.0 | 5.7 | 7.0 |
| 'Common' | 2.0 | 4.0 | 5.0 | 5.0 | 6.0 | 5.3 |
| 'Everest' | 2.7 | 6.7 | 6.7 | 7.3 | 7.0 | 7.0 |
| 'Everglade' | 2.3 | 6.3 | 7.0 | 7.3 | 7.3 | 6.7 |
| 'Impact' | 2.7 | 6.0 | 7.0 | 6.7 | 6.3 | 7.0 |
| 'Kenblue' | 2.0 | 4.0 | 4.7 | 4.3 | 4.3 | 5.0 |
| 'Liberator' | 4.3 | 7.0 | 7.7 | 7.7 | 6.7 | 7.3 |
| 'Limousine' | 4.0 | 6.3 | 6.3 | 6.7 | 6.7 | 7.3 |
| 'Midnight' | 2.0 | 3.7 | 4.3 | 4.0 | 4.0 | 4.7 |
| 'NuBlue' | 4.3 | 6.0 | 6.0 | 6.0 | 6.0 | 7.3 |
| 'NuDensity' | 4.0 | 6.0 | 6.7 | 7.0 | 7.0 | 6.3 |
| 'NuGlade' | 2.7 | 6.0 | 6.7 | 7.3 | 6.7 | 7.7 |
| 'Park' | 1.0 | 3.7 | 4.7 | 4.3 | 4.7 | 5.3 |
| 'Perfection' | 2.7 | 7.0 | 7.3 | 7.7 | 6.7 | 7.3 |
| 'Princeton P-105' | 2.7 | 5.0 | 5.3 | 4.7 | 5.0 | 6.7 |
| 'Rambo' | 3.0 | 6.3 | 7.3 | 7.3 | 6.0 | 7.0 |
| 'Rugby II' | 2.3 | 5.7 | 5.7 | 5.7 | 5.7 | 6.0 |
| 'Total Eclipse' | 3.3 | 6.7 | 7.0 | 6.7 | 6.3 | 7.3 |
| 'Tsunami' | 3.0 | 6.3 | 7.3 | 8.0 | 7.0 | 7.7 |
| LSD (5%) | 0.6 | 0.6 | 0.6 | 0.7 | 0.9 | 0.6 |

Density visual rating: 1-9 (1 = least dense and 9 = most dense)
Quality visual ratings: 1-9 (1 = lowest quality and 9 = highest quality)

TABLE 6

Mean turfgrass spring green-up, density, and quality ratings for Kentucky bluegrass cultivar evaluation. Data are from 2008.

| | Spring | Density | | Quality | | |
|---|---|---|---|---|---|---|
| Cultivar | Green-up | Spring | Summer | May | Jun. | Jul. |
| 'Absolute' | 7.0 | 8.0 | 7.0 | 6.3 | 6.7 | 6.3 |
| 'NE-KYB-05-001' | 8.3 | 8.7 | 8.3 | 7.7 | 7.3 | 6.0 |
| 'Blue Chip' | 7.0 | 8.0 | 7.0 | 5.7 | 4.7 | 5.3 |
| 'Blue Moon' | 6.3 | 8.0 | 6.3 | 6.7 | 6.7 | 6.7 |
| 'Caliber' | 7.3 | 7.3 | 7.3 | 4.7 | 3.0 | 5.0 |
| 'Common' | 6.3 | 7.7 | 6.3 | 4.3 | 2.7 | 4.0 |
| 'Everest' | 6.7 | 8.3 | 6.7 | 6.7 | 7.0 | 6.7 |
| 'Everglade' | 6.7 | 8.0 | 6.7 | 7.0 | 5.7 | 6.0 |
| 'Impact' | 7.0 | 8.3 | 7.0 | 6.7 | 7.0 | 6.7 |
| 'Kenblue' | 5.0 | 6.0 | 5.0 | 4.0 | 2.7 | 4.0 |
| 'Liberator' | 7.7 | 8.3 | 7.7 | 6.7 | 6.3 | 7.0 |
| 'Limousine' | 7.7 | 8.7 | 7.7 | 5.7 | 5.3 | 4.3 |
| 'Midnight' | 5.7 | 6.0 | 5.7 | 3.7 | 2.3 | 4.0 |
| 'NuBlue' | 7.3 | 7.7 | 7.3 | 5.3 | 3.7 | 5.3 |
| 'NuDensity' | 7.3 | 8.7 | 7.3 | 7.0 | 7.0 | 7.3 |
| 'NuGlade' | 6.3 | 8.0 | 6.3 | 6.7 | 6.0 | 5.7 |
| 'Park' | 7.3 | 7.7 | 7.3 | 4.0 | 2.0 | 4.0 |
| 'Perfection' | 6.3 | 8.3 | 6.3 | 7.0 | 6.7 | 6.7 |
| 'Princeton P-105' | 7.0 | 8.0 | 7.0 | 6.7 | 6.0 | 5.7 |
| 'Rambo' | 7.0 | 8.3 | 7.0 | 7.3 | 7.7 | 7.0 |
| 'Rugby II' | 6.7 | 7.7 | 6.7 | 6.7 | 6.0 | 5.7 |
| 'Total Eclipse' | 7.0 | 7.7 | 7.0 | 6.3 | 6.0 | 6.0 |
| 'Tsunami' | 6.7 | 8.0 | 6.7 | 6.7 | 6.7 | 7.0 |
| LSD (5%) | 0.8 | 0.5 | 0.7 | 0.6 | 0.5 | 0.6 |

Spring Green up visual rating: 1-9 (1 = least green and 9 = most green)
Density visual rating: 1-9 (1 = least dense and 9 = most dense)
Quality visual ratings: 1-9 (1 = lowest quality and 9 = highest quality)

Shade Tolerance

An experiment was initiated in 2006 at a research facility located near Mead, Nebr. with 'NE-KYB-05-001', 'Thermal Blue', and 'Midnight' to compare shade tolerance among these three bluegrasses. Plots were mowed weekly at 2.5 inches and clippings were removed. Plots received 3.0 lbs N per 1000 $ft^2$ per growing season with applications made at 1.0 lbs per 1000 $ft^2$ in May, September, and October. No fungicides or insecticides were applied to the plots. Post emergence herbicides were applied as needed to prevent weed encroachment problems. All 3 varieties were maintained at 60% shade conditions, during the entire experiment. Shade conditions were achieved by using a special shade cloth which provided 60% reduction of incident sunlight.

Figure 2:
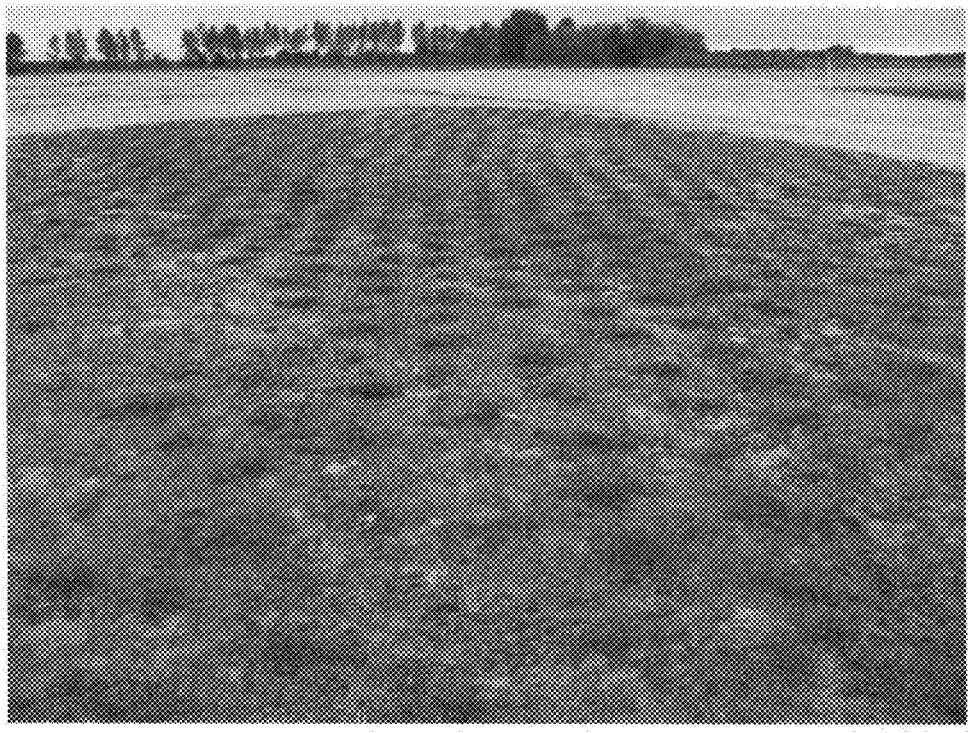
FIG. 2: 'NE-KYB-05-001' field at Newton, Ga. (transition zone 8).
Figure 3:
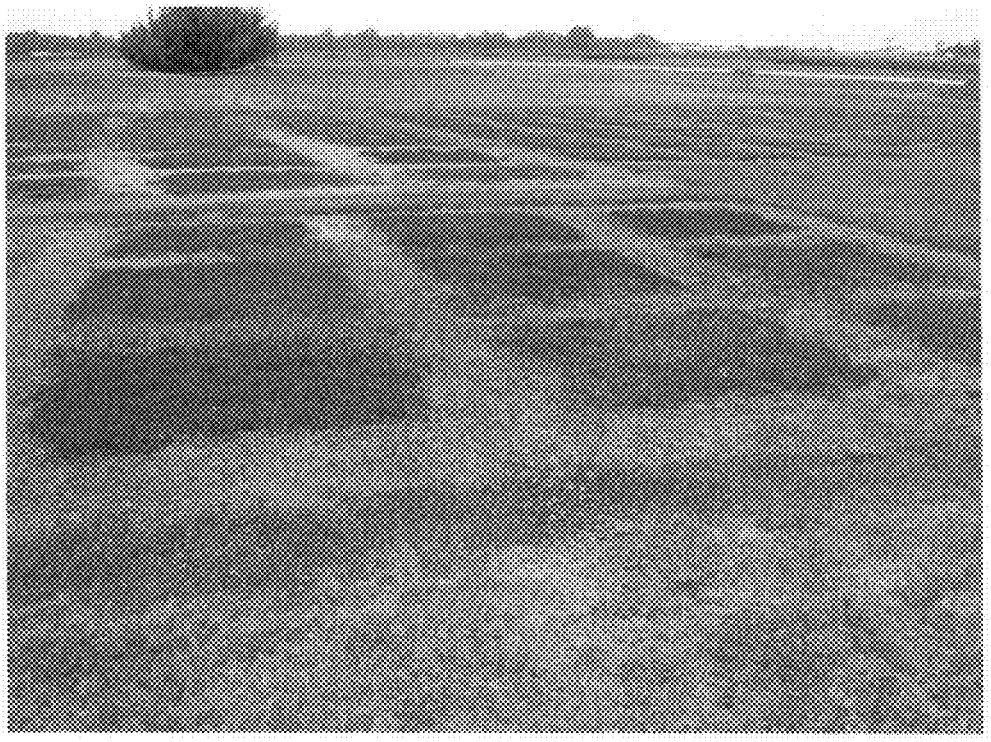
FIG. 3: 'NE-KYB-05-001' test plots, MS. 'NE-KYB-05-001' is first on the left at lower corner, in the center of the plots and at right upper corner.
Figure 4:
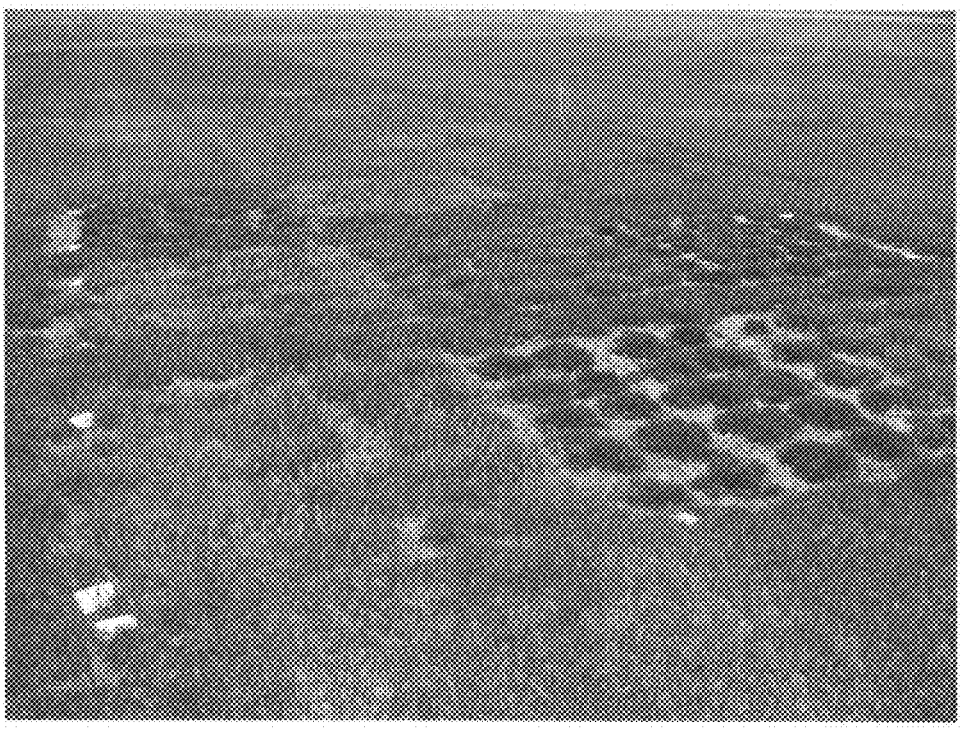
FIG. 4: 'NE-KYB-05-001' test plots at Mead, Nebr. 'NE-KYB-05-001' is on 1st row second to left, 2nd row 3rd from left and 3rd row 1st from left.
Figure 5:
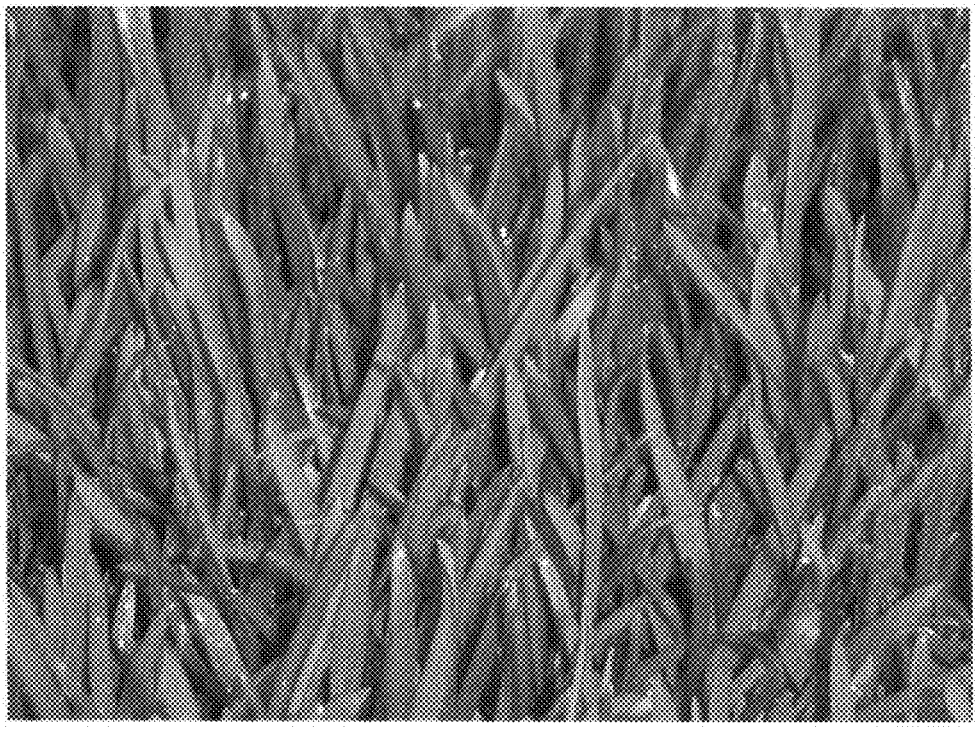
FIG. 5: 'NE-KYB-05-001' close up.
Figure 6:
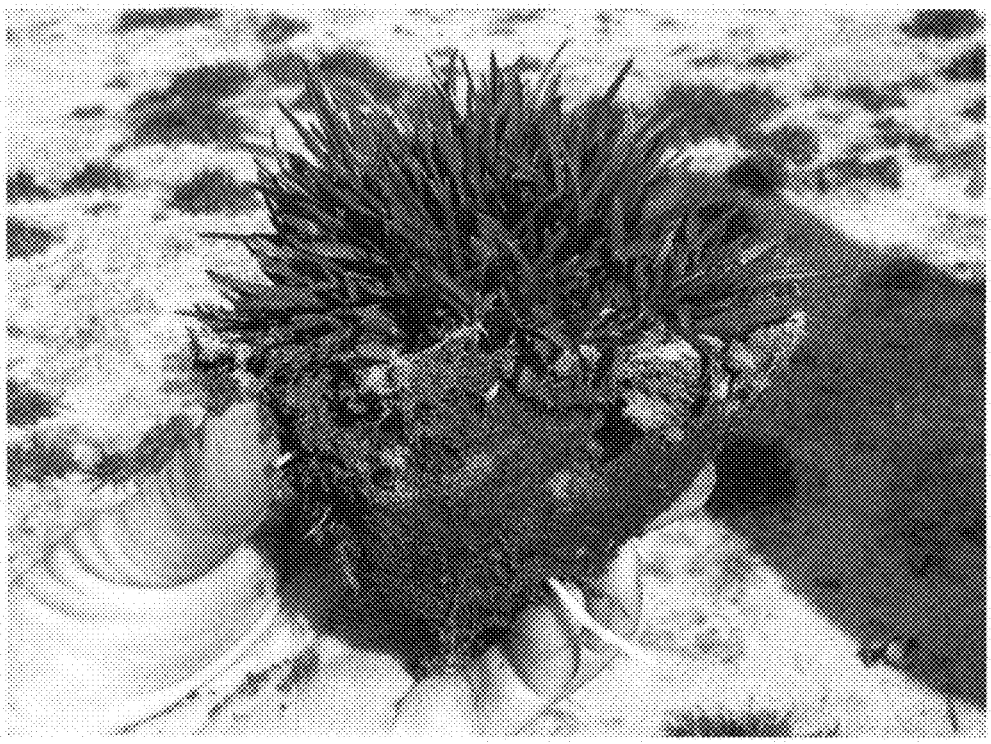
FIG. 6: 'NE-KYB-05-001' plug.
Figure 7:
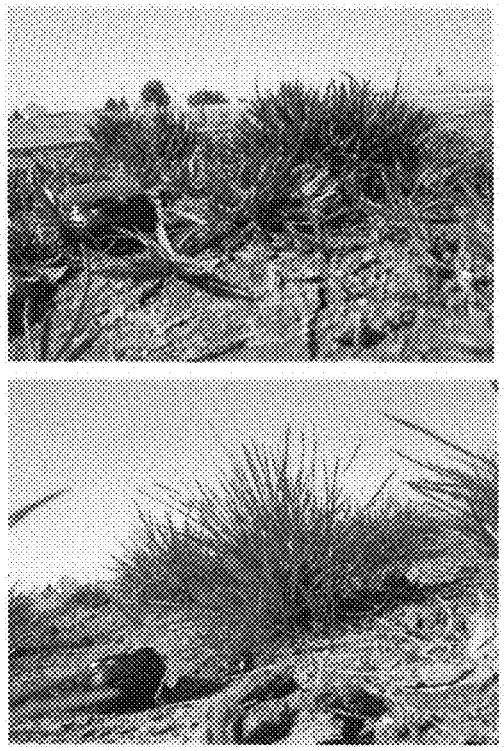
FIG. 7: Plant height comparison: 'NE-KYB-05-001' top; 'Midnight' bottom.

The Analysis of Variance (ANOVA) showed grasses differed significantly at 1% level in spring green-up, color, density and quality when exposed to shade conditions (Table 7). 'NE-KYB-05-001' maintained a darker green color (R.H.S. Colour Chart 135B) than 'Thermal Blue' (R.H.S Colour Chart 143B) or 'Midnight' (R.H.S. Colour Chart 143A); 'NE-KYB-05-001' also greened up earlier than 'Thermal Blue', and 'Midnight' (Table 8). 'NE-KYB-05-001' had superior turfgrass quality and density under the shaded conditions of this study. The higher turfgrass quality was primarily a result of 'NE-KYB-05-001' maintaining darker green color, better density and lower heights than 'Thermal Blue' or 'Midnight' (FIG. 2). Reduced green color and etiolated growth are common responses of plants lacking tolerance to reduced light intensity associated with shaded growing conditions. 'NE-KYB-05-001' demonstrated plant growth responses associated with superior shade tolerance.

TABLE 7

Analysis of variance for three Kentucky bluegrass cultivars grown at 60% shade near Mead, NE. Data are from 2008.

| | | Mean Squares | | | | | | |
|---|---|---|---|---|---|---|---|---|
| | | Spring Green-up | Color | Density | | Quality | | |
| Source | df | Mar. | Jun. | Spring | Summer | May | Jun. | Jul. |
| Rep | 2 | 2.33 | 0.78 | 0.11 | 0.11 | 0.11 | 0.33 | 0.44 |
| Genotypes | 2 | 4.3 ** | 23.11 ** | 5.44 ** | 9.78 ** | 11.44 ** | 17.33 ** | 14.78 ** |
| Error | 4 | 0.17 | 0.11 | 0.11 | 0.11 | 0.11 | 0.17 | 0.28 |
| CV (%) | 5.6 | 8.7 | 4.6 | 5.2 | 5.8 | 7.7 | 10.1 | |

Spring green up visual rating: 1-9 (1 = least green and 9 = most green)
Color visual rating: 1-9 (1 = least green and 9 = most green)
Density visual rating: 1-9 (1 = least dense and 9 = most dense)
Quality visual ratings: 1-9 (1 = lowest quality and 9 = highest quality)
** Significant at the 0.01 level

TABLE 8

Mean turfgrass spring green-up, color, density and quality ratings for three Kentucky bluegrass cultivars grown in a shade evaluation study located near Mead, NE. Plots were maintained under a shade environment of 60% reduction of incident sunlight. Data are from 2008.

| | Mean | | | | | | |
|---|---|---|---|---|---|---|---|
| | Spring Green-up (1-9) | Color (1-9) | Density (1-9) | | Quality (1-9) | | |
| Genotypes | Mar. | Jun. | Spring | Summer | May | Jun. | Jul. |
| 'NE-KYB-05-001' | 8.7 | 8.7 | 8.7 | 8.3 | 8.0 | 8.0 | 7.7 |
| 'Midnight' | 6.3 | 3.3 | 6.0 | 5.0 | 4.3 | 3.3 | 3.3 |
| 'Thermal Blue' | 7.0 | 4.7 | 7.0 | 6.0 | 5.0 | 4.7 | 4.7 |

Spring green up visual rating: 1-9 (1 = least green and 9 = most green)
Color visual rating: 1-9 (1 = least green and 9 = most green)
Density visual rating: 1-9 (1 = least dense and 9 = most dense)
Quality visual ratings: 1-9 (1 = lowest quality and 9 = highest quality)
Green color according to R.H.S. Colour Chart That which is claimed is:

1. A new and distinct variety of Kentucky bluegrass plant named 'NE-KYB-05-001', as herein illustrated and described, characterized by its distinctive and unique combination of several characteristics such as: exclusively vegetative propagation, dark green foliage, shorter leaf length, improved shade and drought tolerance and slow vertical growth habit.

* * * * *